United States Patent
Kiraly et al.

(10) Patent No.: US 10,258,304 B1
(45) Date of Patent: Apr. 16, 2019

(54) METHOD AND SYSTEM FOR ACCURATE BOUNDARY DELINEATION OF TUBULAR STRUCTURES IN MEDICAL IMAGES USING INFINITELY RECURRENT NEURAL NETWORKS

(71) Applicant: Siemens Healthcare GmbH, Erlangen (DE)

(72) Inventors: Atilla Peter Kiraly, San Jose, CA (US); Carol L. Novak, Newtown, PA (US); Benjamin L. Odry, West New York, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 27 days.

(21) Appl. No.: 15/825,304

(22) Filed: Nov. 29, 2017

(51) Int. Cl.
| | | |
|---|---|---|
| *G06K 9/00* | (2006.01) | |
| *A61B 6/00* | (2006.01) | |
| *A61B 6/03* | (2006.01) | |
| *A61B 5/08* | (2006.01) | |
| *A61B 5/00* | (2006.01) | |
| *G06T 7/13* | (2017.01) | |
| *G06T 7/11* | (2017.01) | |

(Continued)

(52) U.S. Cl.
CPC ............. *A61B 6/5217* (2013.01); *A61B 5/08* (2013.01); *A61B 5/7267* (2013.01); *A61B 6/032* (2013.01); *A61B 6/504* (2013.01); *G06K 9/6256* (2013.01); *G06N 3/0445* (2013.01); *G06N 3/08* (2013.01); *G06T 7/0014* (2013.01); *G06T 7/11* (2017.01); *G06T 7/13* (2017.01); *G06T 2200/04* (2013.01); *G06T 2207/10081* (2013.01); *G06T 2207/20021* (2013.01); *G06T 2207/30101* (2013.01)

(58) Field of Classification Search
None
See application file for complete search history.

(56) References Cited

U.S. PATENT DOCUMENTS

| 7,116,810 B2 | 10/2006 | Miller et al. |
| 7,953,266 B2 | 5/2011 | Gulsun et al. |

(Continued)

OTHER PUBLICATIONS

Saba et al. Maximizing Quantitative Accuracy of Lung Airway Lumen and Wall Measures Obtained from X-ray CT Imaging, J Appl Physiol 95, May 16, 2003, pp. 1063-1075.

(Continued)

*Primary Examiner* — Atiba O Fitzpatrick

(57) ABSTRACT

A method and apparatus for automated boundary delineation of a tubular structure in a 3D medical image of a patient using an infinitely recurrent neural network (IRNN) is disclosed. An unraveled cross-section image corresponding to a portion of a tubular structure is extracted from 3D medical image. The unraveled cross-section image is divided into a plurality of image chunks. A boundary of the portion of the tubular structure is detected based on the plurality of image chunks using a trained IRNN. The trained IRNN repeatedly inputs a sequential data stream, including the plurality of image chunks of the unraveled cross-section image, for a plurality of iterations while preserving a memory state between iterations, and detects, for each image chunk of the unraveled cross-section image input to the trained IRNN in the sequential data stream, a corresponding section of the boundary of the portion of the tubular structure.

25 Claims, 4 Drawing Sheets

(51) Int. Cl.
*G06T 7/00* (2017.01)
*G06K 9/62* (2006.01)
*G06N 3/04* (2006.01)
*G06N 3/08* (2006.01)

(56) References Cited

U.S. PATENT DOCUMENTS

| | | |
|---|---|---|
| 8,019,140 B2 | 9/2011 | Odry et al. |
| 8,050,470 B2 | 11/2011 | Coenen et al. |
| 8,290,247 B2 | 10/2012 | Slabaugh et al. |
| 9,129,419 B2 | 9/2015 | Vanhoecke |
| 9,767,557 B1 | 9/2017 | Gulsun et al. |
| 2011/0071383 A1 | 3/2011 | Novak et al. |
| 2017/0079603 A1 | 3/2017 | Novak et al. |
| 2017/0206662 A1 | 7/2017 | Wang et al. |
| 2017/0258433 A1* | 9/2017 | Gulsun ............ A61B 6/5217 |

OTHER PUBLICATIONS

Odry, et al., Active Contour Approach for Accurate Quantitative Airway Analysis, Progress in Biomedical Optics and Imaging—Proceedings of SPIE, (2008); 6916, 12 pgs.

Itu et al., A Machine-Learning Approach for Computation of Fractional Flow Reserve from Coronary Computed Tomography, Journal of Applied Physiology, Article in Press, Apr. 14, 2016, pp. 42-52.

Kiraly et al., Virtual Bronchoscopy for Quantitative Airway Analysis, SPIE 5746, Medical Imaging 2005: Physiology, Function, and Structure from Medical Images, Apr. 14, 2005.

Kiraly et al., Boundary-Specific Cost Functions for Quantitative Airway Analysis, Medical Imaging Computing and Computer-Assisted Intervention—MICCAI; (2007) vol. 4791 of the series Lecture Notes in Computer Science, pp. 784-791.

* cited by examiner

METHOD AND SYSTEM FOR ACCURATE BOUNDARY DELINEATION OF TUBULAR STRUCTURES IN MEDICAL IMAGES USING INFINITELY RECURRENT NEURAL NETWORKS

BACKGROUND OF THE INVENTION

The present invention relates to boundary delineation of tubular structures in medical images, and more particularly, to boundary delineation of tubular structures in medical images using infinitely recurrent neural networks.

Accurate boundary delineation of tubular anatomical structures, such as airways and vessels, is important in order to obtain quantitative measurements for a wide variety of clinical scenarios. For example, in one such scenario, boundary delineation of airways in computed tomography (CT) images can be used for analyzing Chronic Obstructive Pulmonary Disorder (COPD). COPD is a disease that is both common (number three killer in the United States) and chronic, due to few curative treatments. As such, methods to diagnose COPD and monitor the effectiveness of treatments are highly relevant for physicians. An important sub-type of COPD is airway-predominant disease, where the airway walls and/or lumens are thickened due to chronic inflammation. In another scenario, boundary delineation of coronary arteries in medical image data, such as CT, is important for computational fluid dynamics (CFD) in coronary angiography cases.

The large amount of data in a CT scan presents the possibility of precise quantification of disease severity and changes, but requires automation to make this feasible. Automated quantification of airway diseases is especially problematic as the boundaries of airways in CT images may be "fuzzy" and hard to detect by conventional algorithms. In addition, nearby structures can lead to errors in defining the boundaries. When CFD is applied to vascular cases, precise delineation of vascular boundaries is critical for accurate CFD computations. In both of the above described clinical scenarios, a more accurate method for computer-based automated boundary delineation is desirable.

BRIEF SUMMARY OF THE INVENTION

The present invention provides a method and system for automated computer-based boundary delineation of tubular structures in medical images. Embodiments of the present invention provide a data-driven machine-learning based method to perform robust and accurate delineation of anatomical boundaries of tubular structures in medical images.

In one embodiment of the present invention, an unraveled cross-section image corresponding to a portion of a tubular structure is extracted from 3D medical image of a patient. The unraveled cross-section image is divided into a plurality of image chunks. A boundary of the portion of the tubular structure is detected based on the plurality of image chunks using a trained infinitely recurrent neural network. The trained infinitely recurrent neural network repeatedly inputs a sequential data stream including the plurality of image chunks of the unraveled cross-section image, for a plurality of iterations, while preserving a memory state between iterations. The trained infinitely recurrent neural network detects, for each image chunk of the unraveled cross-section image input, a corresponding section of the boundary of the portion of the tubular structure.

These and other advantages of the invention will be apparent to those of ordinary skill in the art by reference to the following detailed description and the accompanying drawings.

DETAILED DESCRIPTION

Figure 1:
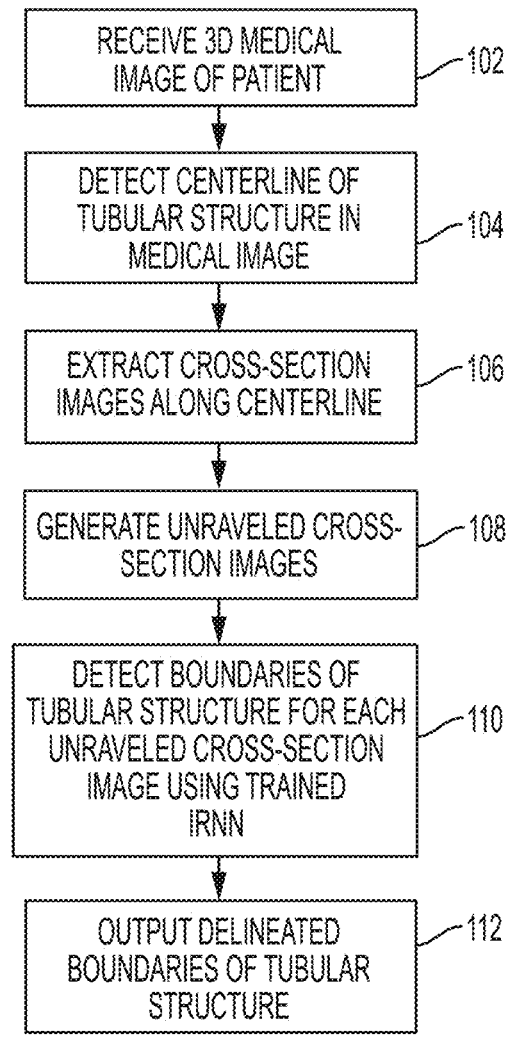
FIG. 1 illustrates a method for automated boundary delineation of a tubular structure of a patient in a 3D medical image according to an embodiment of the present invention.

The present invention relates to a method and system for automated computer-based boundary delineation of tubular structures in medical images. Embodiments of the present invention are described herein to give a visual understanding of the method for automated boundary delineation of tubular structures. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Embodiments of the present invention provide a data-driven method to perform robust and accurate delineation of anatomic boundaries of tubular structures in 3D medical images using a new deep learning architecture referred to herein as an infinitely recurrent neural network (IRNN). Previous approaches for computer-based boundary delineation of tubular structures use machine learning techniques to perform the structure detection, but ultimately the boundary delineation is performed by traditional computer vision means. Embodiments of the present invention provide automated boundary delineation of tubular structures in 3D medical images with improved accuracy as compared with previous approaches.

Recurrent neural networks (RNN) are a type of deep neural network in which the same learned weights are applied over a subset of variable-length input. RNNs have typically been used for prediction tasks from sequential information with multiple time points. For example, RNNs have previously been successfully applied for natural language processing and video processing. In these cases, words (natural language processing) or frames (video processing) are sequentially passed through the network to arrive at an output for each input. In these applications, the recurrence is singular as the network handles only the current frame (or word) and the one immediately previous. According to an advantageous aspect of the present invention, rather than applying the network to a single stream of data, embodiments of the present invention repeatedly input the entire data stream to an RNN to create an "infinite" stream of data to allow for an arbitrary number p of feed forward or back-propagation operations. Although the repeating data stream is referred to herein an "infinite", and the RNN trained to input such a repeating data stream and output tubular structure boundaries for each input is referred to herein as an infinitely recurrent neural network (IRNN), it is to be understood that in practice, the input data stream will not be repeated infinitely. In practice, the value of p will be assigned a specific value and the number of iterations through the data stream for training and application will be capped at that value.

FIG. 1 illustrates a method for automated boundary delineation of a tubular structure of a patient in a 3D medical image according to an embodiment of the present invention. In an exemplary embodiment, the method of FIG. 1 can be used to perform automated boundary delineation of an airway in a 3D medical image, such as a 3D computed tomography (CT) image. In another exemplary embodiment, the method of FIG. 1 can be used to perform automated boundary delineation of a vascular structure, such as a coronary artery or other type of artery, in a 3D medical image, such as a 3D CT image or a 3D computed tomography angiography (CTA) image.

At step 102, a 3D medical image of the patient is received. The 3D medical image of the patient includes at least one tubular structure of interest of the patient, such as an airway or vessel (e.g., coronary artery, renal artery, cerebral artery, etc.). In an exemplary embodiment, the 3D medical image is a CT image or a CTA image, but the present invention is not limited thereto and the 3D medical image may be acquired using any type of medical imaging modality (e.g., CT, magnetic resonance imaging [MRI], ultrasound, positron emission tomography [PET], etc.). The 3D medical image can be received directly from an image acquisition device, such as a CT scanner, or can be received by loading a previously stored 3D medical image of the patient.

At step 104, a centerline of a tubular structure of interest is detected in the 3D medical image. In an advantageous implementation, the centerline of the tubular structure is automatically detected in the 3D medical image, for example using a centerline tracing method or a machine learning based centerline detection method. For example, airway centerline detection can be performed using a tree model from an initial bronchial tree segmentation, as described in U.S. Pat. No. 8,019,140, entitled "System and Method for Determining a Size of an Airway Lumen and a Thickness of an Airway Wall", and United States Patent Publication No. 2017/0079603, entitled "Visualizing Different Types of Airway Wall Abnormalities", which are herein incorporated by reference in their entirety. Vessel centerline detection can be performed using a combined model-driven and data-driven method, as described in U.S. Pat. No. 9,129,417, entitled "Method and System for Coronary Artery Centerline Extraction", which is incorporated herein by reference in its entirety. Alternatively, the vessel centerline detecting can be performed using the method described in U.S. Pat. No. 7,953,266, entitled "Robust Vessel Tree Modeling", which is incorporated herein by reference in its entirety. Other automatic or semi-automatic techniques for extracting airway or vessel centerlines may be used as well. In another possible implementation, the centerline of the tubular structure may be manually annotated by a user using a user input device, such as a mouse.

At step 106, cross-section images are extracted from the 3D medical image along the centerline of the tubular structure. In one embodiment, the cross-section images are 2D cross section images that are extracted from the 3D medical image at a plurality of sampling points along the centerline of the tubular structure. In this case, the centerline of the tubular structure is sampled to establish a plurality of sample points along the centerline. A uniform sampling distribution may be used to define evenly spaced sampling points, but the present invention is not limited thereto and other possible sampling distributions may be used depending on the tubular structure of interest. A respective 2D cross-section image is extracted from the 3D medical image at each sampling point on the centerline of the tubular structure. Each 2D cross-section image can be a predetermined size image centered at the respective sampling point and aligned with a tangent to the vessel centerline at that sampling point.

In another embodiment, the cross-section images are 3D volumetric cross-section images (i.e., sub-volumes), each extracted from the 3D medical image along a length of the centerline. For example, the centerline of an airway branch or a vessel branch can be divided into sections of a certain length, and a corresponding 3D volumetric cross-section image can be extracted for each section of the centerline. Alternatively, a single 3D volumetric cross-section image can be extracted along an entire length of an airway or vessel branch. The 3D volumetric cross-section image for a particular section of the centerline can be extracted by extracting a predetermined sized 3D sub-volume that is centered on the centerline and aligned with the centerline and a tangent of the centerline. The 3D volumetric cross-section image can be a 3D tube or cylinder volume that is aligned with and centered on the corresponding section of the centerline and has a predetermined radius surrounding the corresponding section of the centerline.

At step 108, unraveled cross-section images are generated from the cross-section images extracted from the 3D medical image. In the embodiment in which the cross-section images are 2D cross-section images, a corresponding 2D unraveled cross-section image is generated from each 2D cross-section image. The 2D unraveled cross-section image is generated by unraveling the 2D cross-section image about the centerline point at which the 2D cross-section image is centered. In particular, a given 2D cross-section image is unraveled about the centerline point by reformatting a circular region having a predetermined radius (or an annular region having predetermined inner and outer radii) around the centerline point. The result is a 2D unraveled image in which circular image data at a given radius in the 2D cross-section image is aligned linearly in the 2D unraveled cross-section image. The predetermined radius can be set to be a radius larger than an expected maximum possible thickness of an airway or vessel to ensure that the inner and outer boundaries of the airway or vessel are both included in the 2D unraveled cross-section image. The 2D unraveled image reformats the image data in the circular region of the 2D cross-section image such that the rectangular (x and y) coordinates of the image data in the 2D unraveled image correspond to polar coordinates of the image data in the 2D cross-section image. Accordingly, the x coordinate in the 2D unraveled image represents an angle with respect to the centerline point in the 2D cross-section image and the y coordinate in the 2D unraveled image represents a radius, or distance from the centerline point, in the 2D cross-section image. The 2D unraveled cross-section image is further described below in connection with FIG. 3.

In the embodiment in which the cross-section image is a 3D volumetric cross-section image, a corresponding 3D unraveled cross-section volume is generated from a given 3D volumetric cross-section image. The 3D unraveled cross-section volume is generated by unraveling a 3D tubular/cylindrical region in the 3D volumetric cross-section image about the centerline section along which the 3D tubular/cylindrical region is centered. The 3D tubular region can be a 3D region running along a length of a centerline section and having a predetermined radius (or predetermined inner and outer radii) with respect to the centerline at each point along the centerline section. The predetermined radius can be set to be a radius larger than an expected maximum possible thickness of an airway or vessel to ensure that the inner and outer boundaries of the airway or vessel are both included in the 3D unraveled cross-section volume. It is to be understood that the 3D tubular region can be extracted from a 3D sub volume that was extracted from the 3D medical image or the 3D tubular region can be extracted directly from the 3D medical image. The 3D tubular region is unraveled by reformatting the image data in the 3D tubular region such that two of the coordinates (e.g., x and y coordinates) of the 3D unraveled cross-section volume corresponds to the polar coordinates with respect to a given position on the centerline in the 3D volumetric cross-section image, and the third coordinate (e.g., z coordinate) of the 3D unraveled cross-section volume corresponds to a position along the centerline section. The 3D unraveled cross-section volume is further described below in connection with FIG. 4.

At step 110, boundaries of the tubular structure are detected for each unraveled cross-section image using a trained infinitely recurrent neural network (IRNN). The trained IRNN processes each unraveled cross-section image separately to determine boundaries of the tubular structure in each unraveled cross-section image. For a given unraveled cross-section image, the unraveled cross-section image is divided into sections. Image chunks corresponding to each section are input to the trained IRNN as an input data stream and the trained IRNN outputs detected boundaries for each input image chunk. The input data stream is repeatedly fed to the IRNN while preserving the memory state of the RNN unit between iterations, resulting in a potentially infinite data stream. The trained IRNN updates the predicted boundaries for each image chunk during each iteration of the input data stream. In practice, the number of iterations of the entire input data stream is capped at a predetermined number p. In an advantageous embodiment, for an airway, the IRNN will detect contours for the both inner and outer boundaries of the airway wall. Accordingly, the output boundaries can be used to reevaluate the thickness of the airway walls and lumens. For vessels, the IRNN can similarly detect both the inner and outer vessel walls. It is also possible to configure the IRNN to detect only one of the inner and outer walls of a vessel.

RNNs are a type of deep neural network in which the same learned weights are recursively applied over a subset of a variable-length input. RNNs have typically been used for prediction tasks utilizing sequential information with multiple time points, such as natural language processing or video processing. In these cases, sequential data corresponding to different time points are input to the RNN in a data stream, which predicts an output for each input of the data stream. In these applications, the recurrence is singular, as the RNN handles only the current input and the one immediately previous. There are various types of RNN architectures, such as long short-term memory (LSTM) and gated recurrent unit (GRU).

Figure 2:
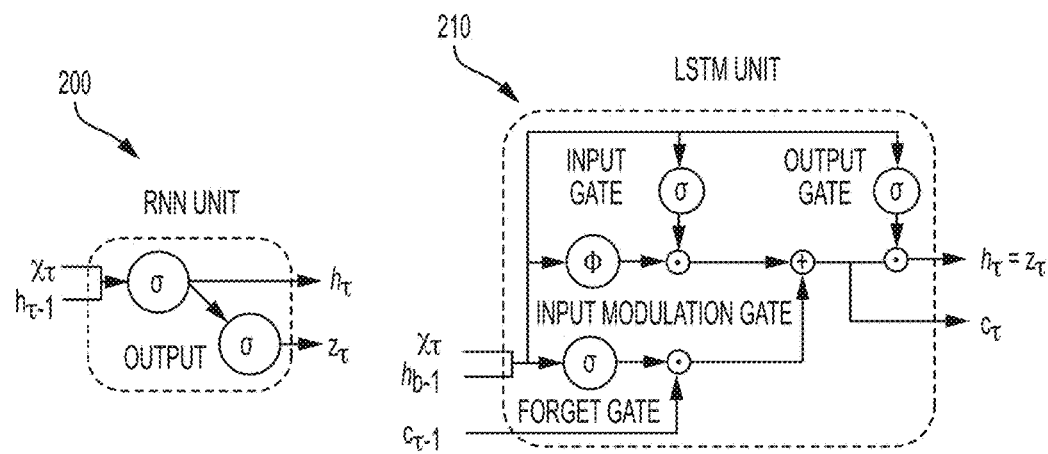
FIG. 2 illustrates an example recurrent neural network (RNN) unit and an example long short-term memory (LSTM) unit.

FIG. 2 illustrates an example RNN unit 200 and an example LSTM unit 210. The RNN unit is recursively applied to sequential data to predict an output for each input. Given an input sequence $[x_1, x_2, \ldots x_T]$, an RNN unit 200 is applied T times to predict an output for each input. Accordingly, given an input sequence $[x_1, x_2, \ldots x_T]$, the RNN can be "unrolled" into an unrolled network that has T layers (RNN units) and each layer (RNN unit) is identical (i.e., each layer shares the same learned weights). After unrolling, an RNN can be trained based on ground truth training samples with back-propagation, similar to a conventional feed-forward neural network. The only difference in the training is that the weights of each copy of the network are averaged to ensure that all copies are identical after the update. As shown in FIG. 2, the RNN unit 200 maps input sequences to hidden states, and hidden states to outputs via the following recurrence equations:

$$h_t = g(W_{xh}x_t + W_{hh}h_{t-1} + b_h)$$
$$z_t = g(W_{hz}h_t + b_z)$$

where g is an element-wise non-linearity such as a sigmoid or hyperbolic tangent, $x_t$ is the input, $h_t \in \mathbb{R}^N$ is the hidden state with N hidden units, and $z_t$ is the output at time t. $W_{xh}$, $W_{hh}$, and $W_{hh}$ are weights and $b_h$ and $b_z$ are biases that are learned in training. As shown in FIG. 1, at time t, the current input $x_t$ and the previous computed hidden state $h_{t-1}$ are input to the RNN unit 100. For a length T input sequence $[x_1, x_2, \ldots x_T]$, the hidden states and outputs are computed sequentially as $h_1$ (letting $h_0=0$), $z_1$, $h_2$, $z_2$, ..., $h_t$, $z_t$.

One challenge for training a traditional RNN is that during the gradient back-propagation phase, the gradient signal can end up being multiplied a large number of times (as many as the number of time steps). This leads to either gradient vanishing (when the magnitude of the gradient signal is smaller than 1) or gradient explosion (when the gradient magnitude is greater than 1). Under gradient vanishing, the network will not be effectively updated; while under gradient explosion, the training process diverges. Therefore, traditional RNN has an issue when training with a long sequence, and thus has a limitation in learning long term memory.

Long Short-Term Memory (LSTM) addresses the long term memory issue of traditional RNN by incorporating memory units that explicitly allow the network to learn when to "forget" previous hidden states and when to update hidden states given new information. LSTM introduces gates which control the input, output, and memory state. As shown in FIG. 2, the LSTM unit 110 includes an input gate 112, an output gate 114, and a forget gate 116, which control the input, output, and memory state, respectively. Suppose at time step $t-1$, the memory state is $c_{t-1}$, the output state/hidden state is $h_{t-1}$, and the input state at time t is $x_t$. The opening or closing of a gate is controlled by a sigmoid function of the current input signal $x_t$ and output signal of the last time point $h_{t-1}$ as follows:

$$i_t = \sigma(W_i x_t + U_i h_{t-1} + b_i),$$
$$f_t = \sigma(W_f x_t + U_f h_{t-1} + b_f),$$
$$o_t = \sigma(W_o x_t + U_o h_{t-1} + b_o),$$

where $i_t$, $f_t$, and $o_t$ are gate functions of the input gate, forget gate, and output gate, respectively, W, U are weights and b is bias, which are learned from a training set. The LSTM unit 110 also includes an input modulation gate 118 that is controlled by a hyperbolic tangent function $g_t$ as follows:

$$g_t = \tan h(W_c x_t + U_c h_{t-1} + b_c).$$

Given the current observation (e.g., the current 2D cross section image in the method of FIG. 2), the memory state $C_t$ will be updated as:

$$C_t = i_t * g_t + f_t * C_{t-1},$$

and the new output/hidden state $h_t$ is:

$$h_t = o_t * \tan h(C_t).$$

According to an advantageous embodiment of the present invention, instead of a time sequence of data, image chunks corresponding to spatial locations in an unraveled cross-section image are input to the RNN/LSTM architecture. Furthermore, according to an advantageous embodiment of the present invention, rather than applying the network to a single stream of data with a beginning and an end, the entire stream of image chunks is repeated while preserving the memory state of the RNN/LSTM. This creates an infinite stream of data to allow for an arbitrary number p of feed forward or back-propagation operations, resulting in an infinitely recurrent neural network (IRNN). It is to be understood that in application the IRNN does not repeat the processing of the data stream infinitely, but the IRNN repeatedly feds the data stream of image chunks to a trained RNN/LSTM unit for a plurality of iterations p. The number of iterations p in training and in application to newly input image data can be capped at a specified maximum value.

Figure 3:
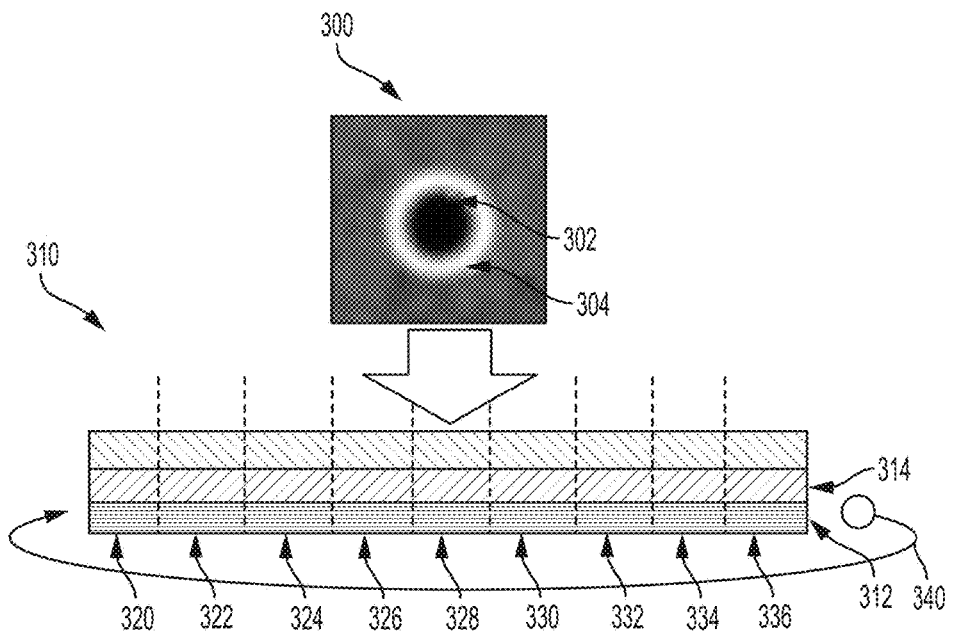
FIG. 3 illustrates an example of creating an infinitely repeating data stream for a 2D unraveled cross-section image of an airway.

FIG. 3 illustrates an example of creating an infinitely repeating data stream for a 2D unraveled cross-section image of an airway. As shown in FIG. 3, a 2D cross-section image 300 of an airway is extracted from a 3D CT volume. The lumen 302 and airway wall 304 of the airway can be observed in the cross-section image 300. A 2D unraveled cross-section image 310 is generated from the 2D cross-section image 300 by unraveling a circular region having a predetermined radius in the 3D cross-section image 300 about the centerline point on which the 3D cross-section image 300 is centered. As shown in FIG. 3, image data located at the same radius with respect to the centerline point in the 2D cross-section image 300 is reformatted as a line in the 2D unraveled cross-section image 310. The lumen 312 and airway wall 314 are unraveled in the 2D unraveled cross-section image 310. The 2D unraveled cross-section image 310 is divided into sections 320, 322, 324, 326, 328, 330, 332, 334, and 336, and each section 320, 322, 324, 326, 328, 330, 332, 334, and 336 is an image patch that is fed to the RNN or LSTM unit. Each section 320, 322, 324, 326, 328, 330, 332, 334, and 336 of the 2D unraveled cross-section image 310 represents an arc length of the airway wall boundaries (inner and outer) in the cross-section image 300, corresponding to a specific range of angles with respect to the centerline point. Accordingly, adjacent image patches of the 2D unraveled cross-section image 310 represent adjacent portions of a circle in the 2D cross-section image 300. As indicated by arrow 340 in FIG. 3, when being processed by the trained IRNN, the image patches corresponding to the sections 320, 322, 324, 326, 328, 330, 332, 334, and 336 of the 2D unraveled cross-section image 310 are repeatedly fed to the RNN/LSTM unit, such that after final image patch 336 of the sequence is fed to the RNN/LSTM unit, the first image patch 320 of the sequence is fed again to the RNN/LSTM unit. The memory state is preserved so that the after the first iteration, image patch 320 is treated as a subsequent input to image patch 336. Since the data repeats at the ends, the supplied input data stream to the RNN/LSTM units is potentially infinite, and therefore can be used to iteratively refine the boundaries detected for each input image patch by the RNN/LSTM unit.

By formatting the airway or vessel data into a sequential dataset, as shown in FIG. 3, the sequential dataset of image patches can be processed using a convolutional RNN or LSTM. This can be similarly applied to any cross-sectional tubular structure. If we think of the airway wall in polar or clock coordinates, it is clear that the position of the airway wall at 2 o'clock needs to be consistent with the position at both 1 o'clock and 3 o'clock to guarantee continuity of results. However, unlike the case of processing streams of words or video frames, where the end of the stream has no direct connection with the beginning of the stream, the circular case of airways means that airway contour position at 1 o'clock should be constrained by the position at 12 o'clock as well as the position at 2 o'clock. When traveling around the circular image data, it is possible to repeat the analysis infinitely until the output boundaries detected at each position converge. This gives rise to the name "infinitely" recurrent neural network. In practice, the processing will usually converge after a few iterations. In an advantageous implementation, a maximum number of iterations can be set and the number of iterations of the entire input data stream can be repeated until the detected boundaries converge or until the maximum number of iterations it reached.

Figure 4:
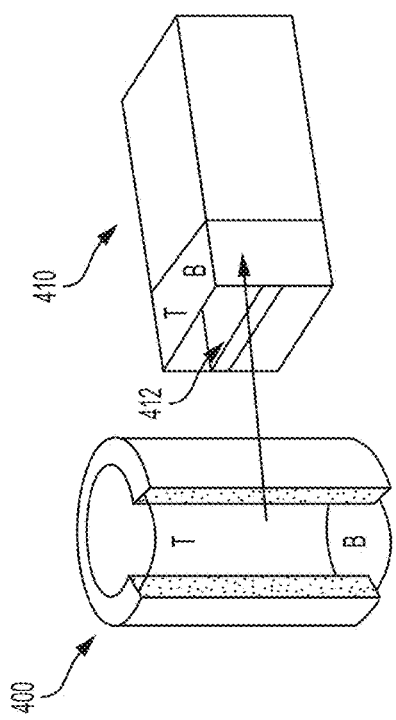
FIG. 4 illustrates an exemplary 3D unraveled cross-section volume.

The generation of an infinite data stream can be similarly performed in a 3D unraveled cross-section volume. FIG. 4 illustrates an exemplary 3D unraveled cross-section volume. As shown in FIG. 4, a 3D tubular region 400 having a predetermined radius around a section of the centerline of a tubular structure is extracted from a 3D medical image. T and B represent a top surface and bottom surface of the 3D tubular region 400, respectively. A 3D unraveled volume 410 is generated from the 3D tubular region 400 by unraveling the 3D tubular region 400 about the centerline. In FIG. 4, the top surface T and bottom surface B of the 3D tubular region 400 can be seen in the 3D unraveled volume 410. The inner and outer boundaries of the tubular structure 412 are then fed to the IRNN by extracting image chunks from the 3D unraveled volume 410 and repeatedly feeding a data stream of the extracted image chunks to an RNN/LSTM unit while preserving the memory state. Each image chunk is a sub volume of the 3D unraveled volume 410 corresponding to respective arc length of the tubular structure along the entire length of the centerline section. For each input image chunk, the IRNN detects the boundaries of the tubular structure for the corresponding arc length over the entire surface of the tubular structure for the centerline section.

Figure 5:
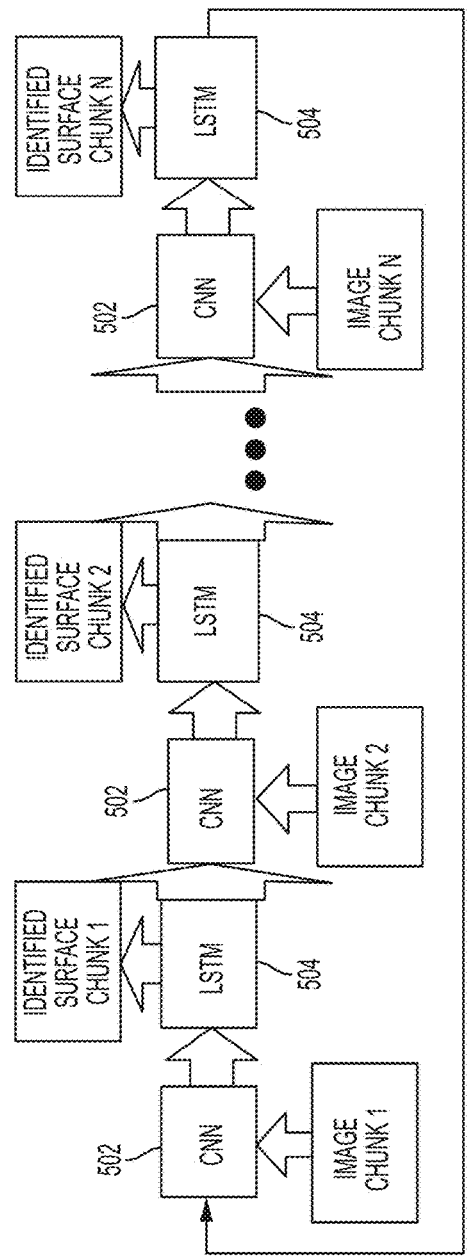
FIG. 5 illustrates implementing an infinitely recurrent neural network (IRNN) using a convolutional LSTM according to an embodiment of the present invention.

In an advantageous embodiment, the IRNN repeatedly feeds the input data stream of image chunks of an unraveled cross-section image into a convolutional RNN or LSTM. FIG. 5 illustrates implementing the IRNN using a convolutional LSTM according to an embodiment of the present invention. Each image chunk (2D or 3D) is fed into a convolutional Neural Network (CNN) 502. The CNN 502 can be any architecture involving combinations of convolutions and max pooling, up-pooling, and deconvolutional kernels. The CNN 502 encodes each input image chunk (i.e., 2D image patch or 3D sub volume) into a feature vector that is a high-level semantic representation of the input image chunk, and the feature vector extracted for each image chunk by the CNN 502 is input to the LSTM unit 504. It is to be understood that the same trained CNN 502 (i.e., having the same learned weights) is applied to each of the image chunks. The LSTM unit 504 may be implemented as shown in FIG. 2. The LSTM unit 504 outputs a computed surface of the airway or vessel wall between inner and outer boundaries via an image or via explicit locations encoded as a series of values per column. In the 2D case, this amounts to a linear series of values describing a surface between the inner and outer boundaries of the tubular structure at a particular cross-section of the tubular structure. In the 3D case, the LSTM unit 504 outputs a 2D series of values describing the surface between the inner and outer boundaries along a particular length of the tubular structure. The identified surface is then passed for processing to the next LSTM, along with the next image chunk. For example, as shown in FIG. 5, image chunk 1 is input to the CNN 502, which encodes image chunk 1 into a feature vector that is input to the LSTM unit 504. The LSTM unit outputs identified surface chunk 1. Image chunk 2 is input to the CNN 502, which encodes image chunk 2 into a feature vector that is input to the LSTM unit 504. The LSTM unit outputs identified surface 2. This process is repeated for all the image chunks in the input data stream, and once an identified surface chunk (identified surface chunk N) is output for the final image chunk in the data stream (Image chunk N), image chunk 1 is input to the CNN 502 again and the process is repeated for the entire data stream for a plurality of iterations, until convergence or until a maximum number of iterations it reached. The memory state of the LSTM unit 504 is preserved over the iterations, so identified surface chunk N is input to the LSTM unit 504 for processing image chunk 1. In another implementation, overlapping image chunks are used to ensure better continuity of the defined surface.

Outputs from carefully selected boundaries of existing approaches can be used to create training data to train the IRNN. In the cases of sub-voxel accuracy, the resampled image can be super-sampled and any additional data such as image resolution and reconstruction kernel can be fed into non-convolutional portions of the network. During training, unlike in conventional deep learning, the back propagation is repeated p times to record changes. Particularly difficult cases or cased deemed important in the training data can be passed through the network additional times as a mechanism to weight these cases more heavily than other training cases. The RNN or LSTM units illustrated in FIG. 1 can include convolutional layers to output a final linear-like boundary that is passed along when the next segment is given. A SegNet architecture can be used where the ground-truth boundary is processed into a Gaussian distribution with the final output being the maximal responses at the distribution.

Returning to FIG. 1, at step 112, the delineated boundaries of the tubular structure are output. The boundaries are detected for each cross-section image using the IRNN in step 110. In the case of 2D cross-section images, each 2D cross-section image is extracted at a respective sampling point along the centerline. Accordingly, detecting of the boundaries of the tubular structure for each 2D cross-section image by the IRNN results in detected boundaries of the tubular structure at each respective sampling point along the centerline. Interpolation can be used to delineate continuous boundaries (inner and outer boundaries) of the tubular structure over the whole length of the tubular structure. The delineated boundaries of the tubular structure can be output by displaying the delineated boundaries on a display device of a computer system. The output delineated boundaries can also be used as input to one or more algorithms for diagnosis, modeling, etc. For example, delineated airway boundaries can be used in an algorithm for automated diagnosis of chronic obstructive pulmonary disorder (COPD). In another example, delineated coronary artery boundaries can be used in an algorithm for performing computational fluid dynamics (CFD) of the heart to obtain accurate CFD results.

Figure 6:
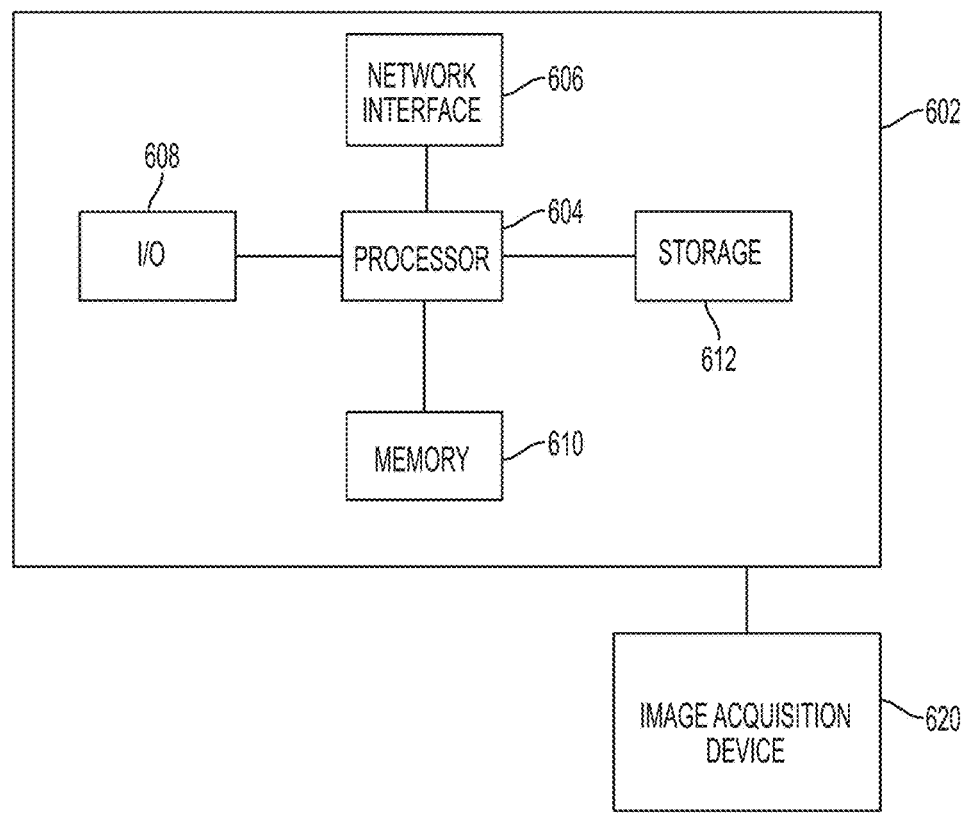
FIG. 6 is a high-level block diagram of a computer capable of implementing the present invention.

The above-described methods for boundary delineation of a tubular structure in 3D medical image using an infinitely recurrent neural network (IRNN) may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIG. 1 may be defined by the computer program instructions stored in the memory 610 and/or storage 612 and controlled by the processor 604 executing the computer program instructions. An image acquisition device 620, such as a CT scanner, can be connected to the computer 602 to input image data to the computer 602. It is possible to implement the image acquisition device 620 and the computer 602 as one device. It is also possible that the image acquisition device 620 and the computer 602 communicate through a network (either wired or wireless). In a possible embodiment, the computer 602 can be located remotely with respect to the image acquisition device 620 and the method steps described herein can be performed as part of a server or cloud based service. In this case, the method steps may be performed on a single computer or distributed between multiple networked computers. The computer 602 also includes one or more network interfaces 606 for communicating with other devices via a network. The computer 602 also includes other input/output devices 608 that enable user interaction with the computer 602 (e.g., display, keyboard, mouse, speakers, microphone, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automated boundary delineation of a tubular structure in a 3D medical image of a patient, comprising:
   extracting, from a 3D medical image of a patient, an unraveled cross-section image corresponding to a portion of a tubular structure in the 3D medical image;
   dividing the unraveled cross-section image into a plurality of image chunks;

detecting a boundary of the portion of the tubular structure based on the plurality of image chunks using a trained infinitely recurrent neural network, wherein the trained infinitely recurrent neural network repeatedly inputs a sequential data stream including the plurality of image chunks of the unraveled cross-section image for a plurality of iterations, while preserving a memory state between iterations, and detects, for each image chunk of the unraveled cross-section image input to the trained infinitely recurrent neural network in the sequential data stream, a corresponding section of the boundary of the portion of the tubular structure.

2. The method of claim 1, wherein extracting, from a 3D medical image of a patient, an unraveled cross-section image corresponding to a portion of a tubular structure in the 3D medical image comprises:
 extracting a 2D cross-section image at a point on a centerline of the tubular structure in the 3D medical image; and
 generating a 2D unraveled cross-section image by unraveling a circular region of the 2D cross-section image having a predetermined radius about the point on the centerline of the tubular structure.

3. The method of claim 2, wherein dividing the unraveled cross-section image into a plurality of image chunks comprises:
 dividing the 2D unraveled cross-section image into a plurality of 2D image patches, each of which corresponds to an arc length of the tubular structure in the 2D cross-section image.

4. The method of claim 3, wherein the trained infinitely recurrent neural network repeatedly inputs a sequential data stream, including the plurality of 2D image patches of the 2D unraveled cross-section image, for a plurality of iterations while preserving a memory state between iterations, and detects, for each 2D image patch of the 2D unraveled cross-section image input to the trained infinitely recurrent neural network in the sequential data stream, a boundary of the corresponding arc length of the tubular structure in the 2D cross-section image.

5. The method of claim 1, wherein extracting, from a 3D medical image of a patient, an unraveled cross-section image corresponding to a portion of a tubular structure in the 3D medical image comprises:
 extracting a 3D tubular region including a cross-section of the tubular structure over a certain length of a centerline of the tubular structure in the 3D medical image; and
 generating a 3D unraveled cross-section volume by unraveling the 3D tubular region about the centerline of the tubular structure over the certain length.

6. The method of claim 5, wherein dividing the unraveled cross-section image into a plurality of image chunks comprises:
 dividing the 3D unraveled cross-section volume into a plurality of 3D sub volumes, each of which corresponds to an arc length of the tubular structure over the certain length of the centerline.

7. The method of claim 6, wherein the trained infinitely recurrent neural network repeatedly inputs a sequential data stream, including the plurality of 3D sub volumes of the 3D unraveled cross-section volume, for a plurality of iterations while preserving a memory state between iterations, and detects, for each 3D sub volume of the 3D unraveled cross-section volume input to the trained infinitely recurrent neural network in the sequential data stream, a boundary of the corresponding arc length of the tubular structure over the certain length of the centerline.

8. The method of claim 1, wherein detecting a boundary of the portion of the tubular structure based on the plurality of image chunks using a trained infinitely recurrent neural network comprises:
 detecting an inner boundary and an outer boundary for the portion of the tubular structure based on the plurality of image chunks using the trained infinitely recurrent neural network.

9. The method of claim 8, wherein the trained infinitely recurrent neural network detects, for each image chunk of the unraveled cross-section image input to the trained infinitely recurrent neural network in the sequential data stream, a surface between a corresponding section of the inner boundary of the portion of the tubular structure and a corresponding section of the outer boundary of the portion of the tubular structure.

10. The method of claim 1, wherein the tubular structure is an airway.

11. The method of claim 1, wherein the tubular structure is a vascular structure.

12. An apparatus for automated boundary delineation of a tubular structure in a 3D medical image of a patient, comprising:
 means for extracting, from a 3D medical image of a patient, an unraveled cross-section image corresponding to a portion of a tubular structure in the 3D medical image;
 means for dividing the unraveled cross-section image into a plurality of image chunks; and
 means for detecting a boundary of the portion of the tubular structure based on the plurality of image chunks using a trained infinitely recurrent neural network, wherein the trained infinitely recurrent neural network repeatedly inputs a sequential data stream, including the plurality of image chunks of the unraveled cross-section image, for a plurality of iterations while preserving a memory state between iterations, and detects, for each image chunk of the unraveled cross-section image input to the trained infinitely recurrent neural network in the sequential data stream, a corresponding section of the boundary of the portion of the tubular structure.

13. The apparatus of claim 12, wherein the means for extracting, from a 3D medical image of a patient, an unraveled cross-section image corresponding to a portion of a tubular structure in the 3D medical image comprises:
 means for extracting a 2D cross-section image at a point on a centerline of the tubular structure in the 3D medical image; and
 means for generating a 2D unraveled cross-section image by unraveling a circular region of the 2D cross-section image having a predetermined radius about the point on the centerline of the tubular structure.

14. The apparatus of claim 13, wherein the means for dividing the unraveled cross-section image into a plurality of image chunks comprises:
 means for dividing the 2D unraveled cross-section image into a plurality of 2D image patches, each of which corresponds to an arc length of the tubular structure in the 2D cross-section image.

15. The apparatus of claim 14, wherein the trained infinitely recurrent neural network repeatedly inputs a sequential data stream, including the plurality of 2D image patches of the 2D unraveled cross-section image, for a plurality of iterations while preserving a memory state between iterations, and detects, for each 2D image patch of the 2D unraveled cross-section image input to the trained infinitely recurrent neural network in the sequential data stream, a boundary of the corresponding arc length of the tubular structure in the 2D cross-section image.

16. The apparatus of claim 12, wherein the means for extracting, from a 3D medical image of a patient, an unraveled cross-section image corresponding to a portion of a tubular structure in the 3D medical image comprises:
    means for extracting a 3D tubular region including a cross-section of the tubular structure over a certain length of a centerline of the tubular structure in the 3D medical image; and
    means for generating a 3D unraveled cross-section volume by unraveling the 3D tubular region about the centerline of the tubular structure over the certain length.

17. The apparatus of claim 16, wherein the means for dividing the unraveled cross-section image into a plurality of image chunks comprises:
    means for dividing the 3D unraveled cross-section volume into a plurality of 3D sub volumes, each of which corresponds to an arc length of the tubular structure over the certain length of the centerline.

18. The apparatus of claim 17, wherein the trained infinitely recurrent neural network repeatedly inputs a sequential data stream, including the plurality of 3D sub volumes of the 3D unraveled cross-section volume, for a plurality of iterations while preserving a memory state between iterations, and detects, for each 3D sub volume of the 3D unraveled cross-section volume input to the trained infinitely recurrent neural network in the sequential data stream, a boundary of the corresponding arc length of the tubular structure over the certain length of the centerline.

19. A non-transitory computer readable medium storing computer program instructions for automated boundary delineation of a tubular structure in a 3D medical image of a patient, the computer program instructions when executed by a processor cause the processor to perform operations comprising:
    extracting, from a 3D medical image of a patient, an unraveled cross-section image corresponding to a portion of a tubular structure in the 3D medical image;
    dividing the unraveled cross-section image into a plurality of image chunks;
    detecting a boundary of the portion of the tubular structure based on the plurality of image chunks using a trained infinitely recurrent neural network, wherein the trained infinitely recurrent neural network repeatedly inputs a sequential data stream, including the plurality of image chunks of the unraveled cross-section image, for a plurality of iterations while preserving a memory state between iterations, and detects, for each image chunk of the unraveled cross-section image input to the trained infinitely recurrent neural network in the sequential data stream, a corresponding section of the boundary of the portion of the tubular structure.

20. The non-transitory computer readable medium of claim 19, wherein extracting, from a 3D medical image of a patient, an unraveled cross-section image corresponding to a portion of a tubular structure in the 3D medical image comprises:
    extracting a 2D cross-section image at a point on a centerline of the tubular structure in the 3D medical image; and
    generating a 2D unraveled cross-section image by unraveling a circular region of the 2D cross-section image having a predetermined radius about the point on the centerline of the tubular structure.

21. The non-transitory computer readable medium of claim 20, wherein dividing the unraveled cross-section image into a plurality of image chunks comprises:
    dividing the 2D unraveled cross-section image into a plurality of 2D image patches, each of which corresponds to an arc length of the tubular structure in the 2D cross-section image.

22. The non-transitory computer readable medium of claim 21, wherein the trained infinitely recurrent neural network repeatedly inputs a sequential data stream, including the plurality of 2D image patches of the 2D unraveled cross-section image, for a plurality of iterations while preserving a memory state between iterations, and detects, for each 2D image patch of the 2D unraveled cross-section image input to the trained infinitely recurrent neural network in the sequential data stream, a boundary of the corresponding arc length of the tubular structure in the 2D cross-section image.

23. The non-transitory computer readable medium of claim 19, wherein extracting, from a 3D medical image of a patient, an unraveled cross-section image corresponding to a portion of a tubular structure in the 3D medical image comprises:
    extracting a 3D tubular region including a cross-section of the tubular structure over a certain length of a centerline of the tubular structure in the 3D medical image; and
    generating a 3D unraveled cross-section volume by unraveling the 3D tubular region about the centerline of the tubular structure over the certain length.

24. The non-transitory computer readable medium of claim 23, wherein dividing the unraveled cross-section image into a plurality of image chunks comprises:
    dividing the 3D unraveled cross-section volume into a plurality of 3D sub volumes, each of which corresponds to an arc length of the tubular structure over the certain length of the centerline.

25. The non-transitory computer readable medium of claim 24, wherein the trained infinitely recurrent neural network repeatedly inputs a sequential data stream, including the plurality of 3D sub volumes of the 3D unraveled cross-section volume, for a plurality of iterations while preserving a memory state between iterations, and detects, for each 3D sub volume of the 3D unraveled cross-section volume input to the trained infinitely recurrent neural network in the sequential data stream, a boundary of the corresponding arc length of the tubular structure over the certain length of the centerline.

* * * * *